United States Patent
Sharma et al.

(10) Patent No.: US 11,419,872 B2
(45) Date of Patent: Aug. 23, 2022

(54) PHOSPHOINOSITIDE 3-KINASE AND SRC INHIBITORS FOR TREATMENT OF PANCREATIC CANCER

(71) Applicant: Innoplexus AG, Eschborn (DE)

(72) Inventors: Om Sharma, Maharashtra (IN); Vijay Singh, Uttar Pradesh (IN); Manoj Kumar, District—Bhagalpur (IN); Ishita Mallick, Pune (IN); Amit Choudhari, Pune (IN); Pulkit Anupam Srivastava, Uttar Prasdesh (IN); Deepak Sharma, Jaipur (IN); Vivekanand Patil, Satara (IN); Priyam Singh, Jharkhand (IN); Adity Shandilya, Bemetara Chhattisgarh (IN); Dinesh Solanke, Nagpur (IN)

(73) Assignee: Innoplexus AG, Eschborn (DE)

( * ) Notice: Subject to any disclaimer, the term of this patent is extended or adjusted under 35 U.S.C. 154(b) by 25 days.

(21) Appl. No.: 16/932,987

(22) Filed: Jul. 20, 2020

(65) Prior Publication Data

US 2022/0016123 A1    Jan. 20, 2022

(51) Int. Cl.
*A61K 31/52* (2006.01)
*A61K 31/496* (2006.01)

(52) U.S. Cl.
CPC ............ *A61K 31/52* (2013.01); *A61K 31/496* (2013.01)

(58) Field of Classification Search
CPC ............................. A61K 31/496; A61K 31/52
See application file for complete search history.

(56) References Cited

FOREIGN PATENT DOCUMENTS

WO    WO 2020/130125    *  6/2020    ............. A61K 47/68

* cited by examiner

*Primary Examiner* — Erich A Leeser
(74) *Attorney, Agent, or Firm* — Ziegler IP Law Group, LLC

(57) ABSTRACT

A phosphoinositide 3-kinase inhibitor for use in the treatment of pancreatic cancer and a method for treatment of pancreatic cancer including administration of an phosphoinositide 3-kinase inhibitor an Src inhibitor to a human subject in need thereof. There is also provided a pharmaceutical composition comprising a phosphoinositide 3-kinase inhibitor and an Src inhibitor.

15 Claims, 2 Drawing Sheets

PHOSPHOINOSITIDE 3-KINASE AND SRC INHIBITORS FOR TREATMENT OF PANCREATIC CANCER

TECHNICAL FIELD

The present disclosure relates generally to treatments of pancreatic cancer; and more specifically, to phosphoinositide 3-kinase inhibitors and an Src inhibitors for use in the treatment of pancreatic cancer and methods for treatment of pancreatic cancer comprising administration of a phosphoinositide 3-kinase inhibitor and an Src inhibitor to a human subject in need thereof. Moreover, the present disclosure relates to a pharmaceutical composition comprising a phosphoinositide 3-kinase inhibitor and an Src inhibitor.

BACKGROUND

Pancreatic cancer is a disease in which malignant cells form in the tissues of the pancreas. The most common type of cancer that forms in the pancreas is pancreatic ductal adenocarcinoma that begins in the cells that line the ducts that carry digestive enzymes out of the pancreas. Pancreatic cancer is rarely detected at its early stages when it is most curable. This is because it often does not cause symptoms until after it has spread to other organs. Pancreatic cancer is largely considered incurable with a one-year relative survival rate at 20%, and a five-year survival rate at 7%.

Generally, pancreatic cancer treatment options are chosen based on the extent of the cancer. Conventional treatment options include surgery, chemotherapy, radiation therapy or a combination of these.

In light of the foregoing discussion, there exists a need for development of better treatment options for pancreatic cancer.

SUMMARY

The present disclosure seeks to provide a treatment of pancreatic cancer.

In one aspect, the present disclosure provides a phosphoinositide 3-kinase inhibitor for use in the treatment of pancreatic cancer, wherein the phosphoinositide 3-kinase inhibitor is for use in combination therapy with an Src inhibitor.

In an important embodiment, the phosphoinositide 3-kinase inhibitor is duvelisib and the Src inhibitor is aripiprazole.

In another aspect, the present disclosure provides a method for treatment of pancreatic cancer comprising administration of an phosphoinositide 3-kinase inhibitor and an Src inhibitor to a human subject in need thereof.

In yet another aspect, the present disclosure provides a pharmaceutical composition comprising a phosphoinositide 3-kinase inhibitor and an Src inhibitor.

In yet another aspect, the present disclosure provides an Src inhibitor for use in the treatment of pancreatic cancer, wherein the Src inhibitor is for use in combination therapy with a phosphoinositide 3-kinase inhibitor.

Additional aspects, advantages, features and objects of the present disclosure would be made apparent from the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

For the purpose of illustrating the present disclosure, exemplary constructions of the disclosure are shown in the drawings. However, the present disclosure is not limited to the specific methods and compounds disclosed herein.

Embodiments of the present disclosure will now be described, by way of example only, with reference to the following diagrams wherein.

DETAILED DESCRIPTION OF EMBODIMENTS

Figure 1:
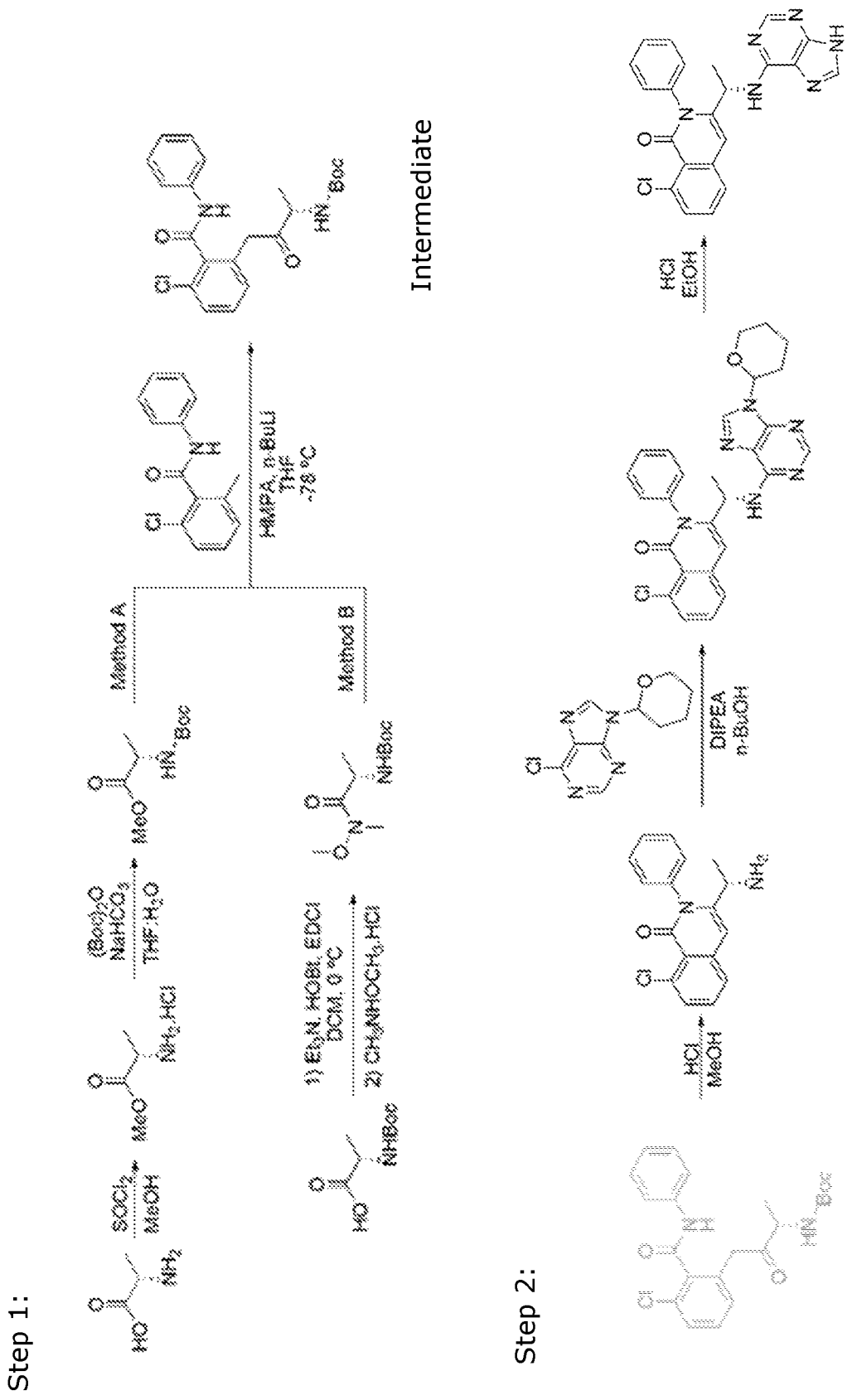
FIG. 1 is an illustration of chemical reactions related to the synthesis of duvelisib, in accordance with an embodiment of the present disclosure.

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, the present disclosure provides a phosphoinositide 3-kinase inhibitor for use in the treatment of pancreatic cancer, wherein the phosphoinositide 3-kinase inhibitor is for use in combination therapy with an Src inhibitor.

In another aspect, the present disclosure provides a method for treatment of pancreatic cancer comprising administration of an phosphoinositide 3-kinase inhibitor and an SRC inhibitor to a human subject in need thereof.

In yet another aspect, the present disclosure provides a pharmaceutical composition comprising a phosphoinositide 3-kinase inhibitor and an Src inhibitor.

In yet another aspect, the present disclosure provides an Src inhibitor for use in the treatment of pancreatic cancer, wherein the Src inhibitor is for use in combination therapy with a phosphoinositide 3-kinase inhibitor.

The present disclosure provides a phosphoinositide 3-kinase (PI3K) inhibitor for use in the treatment of pancreatic cancer. Herein, the term "inhibitor" refers to a substance or agent that is able to inhibit a biological function of a target protein, either by inhibiting the activity or the expression of the target protein. Notably, the term "phosphoinositide 3-kinase inhibitor" refers to the class of therapeutic agents responsible for inhibition of one or more Phosphoinositide 3-kinase (PI3K) enzymes. Phosphoinositide 3-kinases (PI3K) are a well-known family of kinases known to play a role in human disease (for review, see e.g. Fruman et al. (2017) Cell 170:605). PI3K activity is stimulated by diverse oncogenes such as cytoplasmic tyrosine kinases including the Abi gene, Src family, Syk-ZAP-70 family and BTK family, cytoplasmic serine kinases including Raf kinase, cyclin-dependent kinases and growth factor receptors. Said enzymes are a part of the PI3K/AKT/mTOR pathway, specifically, a biological intracellular signalling pathway that inter alia regulates cell growth, proliferation and differentiation. The PI3K family comprises four different classes, namely; Class I, Class II, Class III, Class IV. Specifically, the Class I PI3Ks have a catalytic sub-unit p110, having four types: p110 alpha, p110 beta, p110 gamma and p110 delta. Conventionally, PI3K inhibitors are administered to treat certain cancers, e.g. cancers that either relapsed or unresponsive to other cancer treatments (for review, see e.g. Okkenhaug et al. (2016) Cancer Discov 6:1090).

In an embodiment, the phosphoinositide 3-kinase (PI3K) inhibitor is an inhibitor of the phosphatidylinositol 4,5-bisphosphate 3-kinase catalytic subunit gamma isoform (PIK3CG) and/or an inhibitor of the phosphatidylinositol 4,5-biphosphate 3-kinase catalytic subunit delta isoform (PIK3CD). Suitable assays for determining such inhibition have e.g. been described in Winkler et al. (2013) Chem Biol 20:1364. PIK3CG is responsible for phosphorylation of the phosphoinositides on the 3-hydroxyl group of the inositol ring. Notably, PIK3CG plays an important role in maintenance of the structural integrity of the epithelia. Genetic alterations of PIK3CG have been described. Notably, the most common alterations in PIK3CG are PIK3CG Mutations (1.69%), such as PIK3CG E615K (0.02%), PIK3CG Amplification (0.11%) and PIK3CG Loss (0.03%). Moreover, the PIK3CG is an important modulator of the extracellular signals. The term "modulator" or "modulator of the signal transduction pathway" refers to a compound which is able to modulate the intracellular activity of one or more interacting proteins in a signal transduction pathway.

Optionally, the treatment involves treating a human subject that has higher expression of PIK3CG in tumour pancreatic tissue as compared to non-tumour pancreatic tissue. Herein, the term "expression" refers to gene expression. Notably, gene expression profiling measures or identifies the genes being expressed in a cell at any instance. Gene expression profiling may measure mRNA levels, showing the pattern of genes expressed by a cell at the transcription level or stage. Notably, a human subject with pancreatic cancer to be treated with the PI3K inhibitor and the Src inhibitor may exhibit higher expression of PIK3CG.

There exist several methods to estimate expression levels of PIK3CG including, but not limited to, differential display, serial analysis of gene expression or SAGE, RNA-sequencing, RT-PCR (real-time polymerase chain reaction).

Optionally, the treatment involves treating a subject that carries a mutational PIK3CG variant. Specifically, the PIK3CG mutation identified may be E615K or R839C. The residue Arg 839 is located within the C-terminal catalytic domain. Although this mutation may lead to a loss of function of the enzyme based on X-ray crystal structure, the mutation may result in modulation of p110γ catalytic activity and thus have functional consequences on pancreatic cancer cells. It will be appreciated that phosphoinositide 3-kinases (PI3Ks) regulate several cellular functions that are critical for cancer progression and development, including cell survival, proliferation and migration. Three classes of PI3Ks exist with the class I PI3K encompassing four isoforms of the catalytic subunit known as p110α, p110β, p110γ, and p110δ. Although, p110α was extensively studied previously, recent evidence supports the conclusion that p110β, p110γ, and p110δ can also have a role in cancer. Specifically, p110γ may be involved in several cellular processes associated with cancer. Generally, 3 to 5 percent of pancreatic cancer patients have PIK3CA (phosphatidylinositol-4,5-bisphosphate 3-kinase, catalytic subunit alpha, namely p110α protein) mutations. Although, this subtype does not represent a majority of patients with pancreatic cancer, the tumours of these patients may be exquisitely sensitive to treatments targeting the PI3K pathway In an embodiment, the phosphoinositide 3-kinase (PI3K) inhibitor for use in the treatment of pancreatic cancer is administered as chemotherapy drug. Optionally, the phosphoinositide 3-kinase inhibitor is duvelisib or a salt thereof. Use of duvelisib for treatment of cancers such as such as chronic lymphocytic leukaemia, small lymphocytic lymphoma, follicular lymphoma has been described in the art. Duvelisib is a phosphoinositide 3-kinase inhibitor, specifically of the delta and gamma isoforms of PI3K. In particular, this class of compounds works by preventing PI3K from playing its role in transducing signals from outside of cells into various intracellular pathways involved in cell cycle regulation, apoptosis, DNA repair, senescence, angiogenesis and cell metabolism, including the PI3K/AKT/mTOR pathway. The chemical formula of duvelisib is $C_{22}H_{17}ClN_6O$, the IUPAC name of duvelisib is 8-Chloro-2-phenyl-3-[(1S)-1-(3H-purin-6-ylamino) ethyl]-1(2H)-isoquinolinone and the chemical structure is illustrated in FIG. 1.

Furthermore, synthesis of duvelisib is primarily performed using two different processes. Notably, the two processes differ in a manner of preparing a key intermediate, tert-butyl(S)-4-(3-chloro-2-(phenylcarbamoyl) phenyl)-3-oxobutan-2-ylcarbamate. Upon production of the key intermediate, both the synthesis processes have a common method of obtaining duvelisib. The chemical reactions involved in both the synthesis processes are explained in detail in FIG. 1.

Adverse event analytics was performed with duvelisib and related inhibitors. Duvelisib demonstrated a manageable safety profile in patients with advanced hematologic malignancies. Adverse events reported for duvelisib mainly include diarrhea or colitis, cutaneous reactions, infections and pneumonitis (Cheson et al. (2019) Clin Lymphoma Myeloma Leuk. 19(3): 135-141. Notably, fostamatinib is associated with severe adverse events such as white blood cell disorder, hematological and hepatobiliary disorders (Newland et al. (2017) Immunotherapy 10 (https://doi.org/10.2217/imt-2017-0097)). Also, copanlisib may cause cardiac disorders, glucose metabolism disorders or neurological disorders (Sapon-Cousineau et al. (2020) Curr. Treat. Options in Oncol. 21, 51). Idealisib has been associated with adverse events such as pneumonitis, hematological disorder, diarrhea and colitis (Cuneo et al. (2019) Hematol Oncol 37:3), whereas for deferiprone the most frequently reported adverse effects include joint pain, stiffness or swelling (Taher et al. (1999) Acta Haematol 101:173).

Notably, effects of duvelisib were analyzed on eighty unique crystal structures of PIK3CG, with and without mutations. It was observed that duvelisib has a good binding affinity <−8.5 dock score in all forms of PIK3CG. This demonstrates superior binding affinity and capability of duvelisib with PIK3CG to inhibit the required function.

Optionally, the treatment comprises oral administration of duvelisib or salt thereof. Notably, duvelisib may be administered through the mouth by conventional methods such as oral solutions, tablets, pills, gels, powder, and so forth. Duvelisib is primarily metabolized by CYP3A4, specifically an enzyme present in liver and intestine of human body. Furthermore, duvelisib starts its action 1 to 2 hours after initial administration thereof with an elimination half-life of 5.2 to 10.9 hours.

Optionally, the treatment comprises administration of duvelisib, or salt thereof, at a daily dose of between 10 and 200 mg, such as between 20 and 100 mg, e.g. between 25 and 75 mg. The daily dose of duvelisib or salt thereof can be for example from 10, 15, 20, 25, 30, 35, 40, 45, 50, 55, 60, 65, 70, 75, 80, 85, 90, 95, 100, 110, 120, 130, 140, 150, 160, 170 mg up to 30, 35, 40, 45, 50, 55, 60, 65, 70, 75, 80, 85, 90, 95, 100, 110, 120, 130, 140, 150, 160, 170, 180, 190 or 200 mg.

Optionally, the treatment comprises daily treatment with duvelisib, or salt thereof, over a period of between 7 days and 8 weeks, e.g. between 14 days and 8 weeks, such as between 21 days and 6 weeks. The period of treatment of duvelisib can be for example from 7, 8, 9, 10, 14, 15, 20, 21, 25, 28, 30, 35, 40, 42, 45, 49, 50 days up to 14, 15, 20, 21, 25, 28, 30, 35, 40, 42, 45, 49, 50, 55, 56 days.

Optionally, phosphoinositide 3-kinase inhibitor is selected from a grou comprising at least one of: alpelisib, idelalisib, copanlisib, buparlisib. These inhibitors have been reviewed in Yang, J., Nie, J., Ma, X. et al. Targeting PI3K in cancer: mechanisms and advances in clinical trials. Mol Cancer 18, 26 (2019). More optionally, the treatment comprises administration of duvelisib in combination with another phosphoinositide 3-kinase inhibitor selected from a group comprising at least one of: alpelisib, idelalisib, copanlisib and buparlisib. Alpelisib is an orally bioavailable phosphatidylinositol 3-kinase (PI3K) inhibitor with potential antineoplastic activity. Alpelisib specifically inhibits PI3K in the PI3K/AKT kinase (or protein kinase B) signalling pathway, thereby inhibiting the activation of the PI3K signalling pathway. Alpelisib is preferably used if the cancer has a specific genetic marker such as, an abnormal PIK3CA gene). The IUPAC name of alpelisib is (2S)-1-N[4-methyl-5-[2-(1,1,1-trifluoro-2-methylpropan-2-yl) pyridin-4-yl]-1,3-thiazol-2-yl]pyrrolidine-1,2-dicarboxamide. Moreover, idelalisib is an orally bioavailable, small molecule inhibitor of the delta isoform of the 110 kDa catalytic subunit of class 1 phosphoinositide-3 kinase (PI3K) with potential immunomodulating and antineoplastic activities. Idelalisib inhibits the production of the second messenger phosphatidylinositol-3,4,5-trisphosphate (PIP3), preventing the activation of the PI3K signalling pathway and inhibiting tumour cell proliferation, motility, and survival. The IUPAC name of idelalisib is 5-fluoro-3-phenyl-2-[(1S)-1-(7H-purin-6-ylamino) propyl] quinazolin-4-one. Furthermore, copanlisib is a phosphoinositide 3-kinase (PI3K) inhibitor with potential antineoplastic activity. Notably, copanlisib inhibits the activation of the PI3K signalling pathway, which may result in inhibition of tumour cell growth and survival in susceptible tumour cell populations. The IUPAC name of copanlisib is amino-N-[7-methoxy- 8-(3-morpholin-4-ylpropoxy)-2,3-dihydro-1 H-imidazo [1,2-c]quinazolin-5-ylidene] pyrimidine-5-carboxamide. Lastly, buparlisib is an orally bioavailable specific oral inhibitor of the pan-class 1 phosphatidylinositol 3-kinase (PI3K) family of lipid kinases with potential antineoplastic activity. Buparlisib specifically inhibits class I PI3K in the PI3K/AKT kinase signalling pathway in an ATP-competitive manner, thereby inhibiting the production of the secondary messenger phosphatidylinositol-3,4,5-trisphosphate and activation of the PI3K signalling pathway. The IUPAC name of buparlisib is 5-(2,6-dimorpholin-4-ylpyrimidin-4-yl)-4-(trifluoromethyl) pyridin-2-amine.

As described, the phosphoinositide 3-kinase inhibitor is for use in combination therapy with an Src inhibitor. Herein, the term "combination therapy" refers to the treatment option wherein the patient is administered two or more drugs or therapeutic agents to treat or alleviate symptoms associated with a disease or illness. It will be appreciated that the term combination therapy includes virtually all possible addition techniques and methods between the two or more therapeutic agents, including administration of the two drugs in the same composition or separate administration of the two drugs, either sequentially or simultaneously. The two or more therapeutic agents used in the combination therapy are used in a therapeutically effective amount or in an optimal dose to perform the treatment. It will be appreciated that in combination therapy therapeutically effective amounts administered to the subject may augment the tolerability of the treatment by reducing the effective dosage of each ingredient as opposed to the amount used in their respective monotherapy.

Moreover, the term "Src inhibitor" refers to a class of inhibitors that target the Src kinase family transcribed by proto-oncogenes Src genes. Said proto-oncogenes when altered become oncogenes that contribute to cancer growth. Furthermore, the Src family belongs to non-receptor tyrosine kinases. Proto-oncogene tyrosine-protein kinase Src, also known as proto-oncogene c-Src, or c-Src, is a non-receptor tyrosine kinase protein that in humans is encoded by the SRC gene. Some examples of Src inhibitors include aripiprazole, herbimycin, KX2-391, dasatinib, bosutinib, saracatinib, quercetin and so forth.

Optionally, the Src inhibitor is selected from a group comprising at least one of: aripiprazole, herbimycin, KX2-391, dasatinib, bosutinib and saracatinib. Specifically, herbimycin is a 19-membered macrocyle incorporating a benzoquinone ring and a lactam functionality. It is an ansamycin antibiotic that induces apoptosis and displays anti-tumour effects. The IUPAC name of herbimycin is [(4E,6Z,8S,9S,10E,12S,13R,14S,16S,17R)-8,13,14,17-tetramethoxy-4,10,12,16-tetramethyl-3,20,22-trioxo-2-azabicyclo [16.3.1]docosa-1(21),4,6,10,18-pentaen-9-yl] carbamate. Furthermore, KX2-391 is an orally active Src kinase inhibitor with excellent bioavailability. In pre-clinical animal models, KX2-391 inhibits the growth of both primary tumours and metastasis. The IUPAC name of KX2-391 is N-benzyl-2-[5-[4-(2-morpholin-4-ylethoxy) phenyl] pyridin-2-yl] acetamide. Moreover, dasatinib is an orally bioavailable synthetic small molecule-inhibitor of SRC-family protein-tyrosine kinases. Specifically, dasatinib binds to and inhibits the growth-promoting activities of these kinases. The IUPAC name of dasatinib is N-(2-chloro-6-methylphenyl)-2-[[6-[4-(2-hydroxyethyl) piperazin-1-yl]-2-methylpyrimidin-4-yl] amino]-1,3-thiazole-5-carboxamide. Additionally, bosutinib is a synthetic quinolone derivative and dual kinase inhibitor that targets both Abl and Src kinases with potential antineoplastic activity. Bosutinib inhibits the autophosphorylation of both Abl and Src kinases, resulting in inhibition of cell growth and apoptosis. The IUPAC name of bosutinib is 4-(2,4-dichloro-5-methoxyanilino)-6-methoxy-7[3-(4-methylpiperazin-1-yl) propoxy] quinoline-3-carbonitrile. Furthermore, saracatinib is an orally available 5-, 7-substituted anilinoquinazoline with anti-invasive and anti-tumour activities. This agent binds to and inhibits these tyrosine kinases and affects cell motility, cell migration, adhesion, invasion, proliferation, differentiation, and survival. The IUPAC name is saracatinib is N-(5-chloro-1,3-benzodioxol-4-yl)-7-2-[4-methylpiperazin-1-yl)ethoxy]-5-(oxan-4-yloxy) quinazolin-4-amine.

In a preferred embodiment, the Src inhibitor is aripiprazole or a salt thereof. Aripiprazole is an achiral quinolinone derivative, that possesses a single hydrogen bond donor and five acceptors, has a molecular weight of 448.4 g/mol, and a Log P value of 4.55. The IUPAC name of aripiprazole is 7-[4-[4-(2,3-dichlorophenyl) piperazin-1-yl] butoxy]-3,4-dihydro-1Hquinolin-2-one. The physicochemical properties of aripiprazole comply with Lipinski's rule of five and provide the compound with high bioavailability, protein binding and an acceptable metabolic profile. Aripiprazole is conventionally used to treat certain mental or mood disorders, such as bipolar disorder, schizophrenia, Tourette's syndrome, and irritability associated with autistic disorder. The drug mediates its action by either blocking receptors (antagonist) or by binding to them and inducing an opposite response to receptor's normal role (inverse agonist). Aripiprazole exerts its impact via various receptors including multiple subtypes of serotonin, dopamine, adrenergic, muscarinic acetylcholine and histamine receptors. It also works on serotonin, norepinephrine and dopamine transporter proteins. Several experimental studies have shown that aripiprazole reduced the viability of the glioma cell lines U251 and LN428, the gastric cancer cell line MKN-1, the breast cancer cell line MDA-MB-231, the colon carcinoma cell line CT26, and the human embryonic kidney cell line HEK293 cells. Src is the primary target of aripiprazole in its antitumor action (Kim et al. (2017) Oncotarget 9:5979). Furthermore, aripiprazole treatment induced cell death and accordingly decreased the number of viable cells in the pancreatic cancer cell line PANC-1 (Suzuki et al. (2016) Anticancer Res 36: 5153). The present disclosure, in one embodiment, relates to the use of aripiprazole in combination with a PI3K inhibitor such as duvelisib in the treatment of pancreatic cancer.

Aripiprazole may be synthesized as follows: synthesis begins with alkylation of 7-hydroxy-3,4-dihydro-2(1H)-quinolinone by stirring it with 1,4-dibromobutane (3 molar equivalents) in the presence of potassium carbonate (1 molar equivalents) in dimethylformamide at 60° C. for four hours to give 7-(4-bromobutoxy)-3,4-dihydro-2(1H)-quinolinone. The reaction mixture is then diluted with an equal volume of water, and the organic phase is extracted with ethyl acetate. After rotary evaporation, the resulting product is recrystallized in ethyl alcohol. The product is subsequently combined with sodium iodide (2 molar equivalents) in acetonitrile and refluxed for 30 minutes before cooling to room temperature. Subsequently, 1-(2,3-dichlorophenyl)piperazine (1.5 molar equivalents), and triethylamine (2 molar equivalents.) are added to the reaction mixture, and refluxed for another four hours. The resulting precipitate is filtered and discarded. The filtrate is evaporated in a low-pressure environment, and dissolved in ethyl acetate. Subsequently, the filtrate is washed, dried, and subjected to rotary evaporation to yield a resin. The resin is recrystallized in ethyl alcohol to provide the free base of aripiprazole as a white powdery substance. The powder may then be dissolved in ethyl alcohol with acid to yield a variety of salts. The chemical reactions involved in the synthesis processes of aripiprazole are provided in FIG. 2.

Furthermore, the assay employed to determine a degree of Src inhibition include, but are not limited to, Time-Resolved (Gated) Förster Resonance Energy Transfer (TR-FRET), Fluorescence Assays, Proximity ligation assay. Suitable assays include the c-Src Kinase Inhibitor Screening Assay Kit (DEIABL538) (Creative Diagnostics), the ProFluor® Src-Family Kinase Assay from Promega (Technical Bulletin 6/09, TB331) and the c-Src Kinase Inhibitor Screening Kit from BioVision. Specifically, the TR-FRET technique is widely used for studying kinase assays, cellular signalling pathways, protein-protein interactions, DNA-protein interactions and receptor-ligand binding. Proximity ligation assay (PLA), also referred to as Duolink PLA technology, permits detection of protein-protein interactions in situ (at distances <40 nm) at endogenous protein levels. It exploits specific antibodies identifying (either directly or indirectly) the two proteins of interest and utilizes specific DNA primers covalently linked to the antibodies. A hybridization step followed by DNA amplification with fluorescent probes permit visualization of spots of proximity by fluorescence microscopy.

Optionally, the treatment comprises oral administration of aripiprazole or salt thereof. Notably, aripiprazole may be administered through mouth by conventional methods such as oral solutions, tablets, pills, gels, powder, and so forth. Aripiprazole is primarily metabolized by CYP3A4, specifically an enzyme present in liver and intestine of human body. Furthermore, aripiprazole has an elimination half-life of approximately 75 hours.

Pancreatic cancer patients can be broadly classified under subgroups of age, type of carcinoma and according to the type and severity of treatment received. Furthermore, pancreatic cancer patients can be classified based on at least one of histological type and anatomical position. In one embodiment of the method and uses, the human subject to be treated suffers from a pancreatic cancer selected from the group consisting of: adenocarcinoma of the pancreas, metastatic pancreatic cancer, resectable pancreatic cancer, Stage III pancreatic cancer, Stage IV pancreatic cancer and pancreatic neoplasms.

EXAMPLES

The method described herein employs a tool that employs machine learning and artificial intelligence that identifies connections between drugs, targets, diseases and pathways. The tool enables exploration, detection and management of direct and indirect connections between drugs, targets, diseases and pathways. The tool provides a biological network centred around one of the biological entities (i.e. drug, target, disease or pathway), using enhances natural language processing, statistical scoring approach and entity normalization. The tool uses life science ontologies and identifies potential targets that are yet to be discovered based on the literature and experimental data available around them. Furthermore, the tool analyses druggability and association of a target with respect to a drug and thereafter, computes whether that drug may have a potential possibility of action on such target. The tool is used to analyse multi Omics data with various biological pathways and aids in identifying potential new combinations of drugs and targets, and drugs and pathways. Consequently, diseases relating to such targets and pathways are analysed and such diseases can be potentially related to the drugs that are identified for the targets and pathways.

Herein, several potential drug combinations with a PI3K inhibitor, specifically, duvelisib were analysed to obtain a drug combination that showed favourable results for treatment of pancreatic cancer. Notably, different data sources were identified for pancreatic cancer datasets like the Gene Expression Omnibus (GEO, https://www.ncbi.nlm.nih.gov/geo/) and The Cancer Genome Atlas (TCGA (https://www.cancer.gov/tcga.")) and high throughput sequencing data were downloaded. GEO is a comprehensive library of gene expression in the National Center of Biotechnology Information (NCBI) which is one of the world's largest database of gene chips. Methods of mining the GEO database mainly include the screening of differentially expressed genes, the study of molecular signalling and correlation, and the analysis of gene regulation networks. TOGA is a database of the most large-scale sequencing results, which provides comprehensive cancer genomic datasets on tumour staging, metastasis, survival, patient age, gender and corresponding clinical numbers for researchers. The downloaded data was then normalised and aggregated based on various statistical methods such as log transformation, Robust Multi-array Average, Fragments Per Kilobase Million (FPKM), Transcripts Per Million and the like. Subsequently, top significant differentially regulated genes (DEGs) were identified. The new identified DEGs were treated as features, which were further prioritized based on different Artificial Intelligence and Machine Learning (AI/ML) approaches, such as Random forest, Xgboost and decision tree. Various algorithms such as PageRank, community ranking and Hyper-induced topic search (HITS) were employed to prioritize targets for pancreatic cancer. Newly identified targets were scanned for gene ontology (Molecular Function, Cellular Component and Biological Process), and disease enrichment and pathway enrichment were performed for these targets. Targets that were associated with cancer and with surface cellular compartments were ranked higher and a druggability analysis was performed for each of these targets. Specifically, the drug target mapping was performed for the prioritized target based on target expression pattern in pancreatic cancer. Subsequently, top mapping drugs were listed out for further combination prediction. Multiple permutations and combinations were then generated for each drug and their targets. Subsequently, mechanisms of action of each of the drug were identified and the ranking of the drug combination with its corresponding target was provided based on the mechanism of action. Moreover, a score based on network analysis was performed for each combination of, wherein a drug with a high coverage of a pathway was scored higher. Furthermore, a high number of pathway intersections affected the network analysis-based score negatively. Thereafter, a drug synergy score of a drug-target combination was calculated based on adverse events, toxicity and survival probability. A cumulative score of each drug-target combination was then calculated based on the scores calculated above. An evidence score based on clinical trials, publications and patents mentioning the drug-target combination was calculated and merged with the cumulative score and top scoring combination were thus identified for possible combinations of duvelisib for treatment of pancreatic cancer.

Based on the method outlined above, drugs to be used in combination with the PI3K inhibitor duvelisib were identified. Specifically, drugs such as alitretinoin, gabapentin, clozapine, ziprasidone and several others were analysed. The results were then filtered based on the role of the drug in affecting pancreatic cancer targets, and based on their adverse events and toxicity levels. Aripiprazole, to be used in combination with duvelisib was identified as a highly promising drug. Notably, aripiprazole has 38 targets listed in drug bank including, HTR1, DRD and ADRA family proteins.

DETAILED DESCRIPTION OF THE DRAWINGS

Referring to FIG. 1, illustrated are chemical reactions related to synthesis of duvelisib, in accordance with an embodiment of present disclosure. The synthesis process for duvelisib is a two-step procedure, wherein the first step concludes in formation of an intermediate tert-butyl(S)-4-(3-chloro-2-(phenylcarbamoyl) phenyl)-3-oxobutan-2-yl-carbamate. Subsequently, at step 2, the intermediate is converted to duvelisib.

In particular, at step 1, the intermediate may be obtained using one of a method A or method B. Specifically, in method A, the (S)-2-aminopropanoic acid is reacted with thionyl chloride and anhydrous methanol to form (S)-methyl 2-aminopropanoate hydrochloride. The amine group of (S)-methyl 2-aminopropanoate hydrochloride is protected by its reaction with di-tert-butyl dicarbonate. The protected intermediate is then coupled with the carbanion derived from 2-chloro-6-methyl-N-phenylbenzamide, resulting in the key intermediate. Alternatively in method B, N,O-dimethylhydroxylamine hydrochloride is added to a mixture of (S)-2-(tert-butoxycarbonylamino)propanoic acid, triethylamine, HOBt, EDCI in dichloromethane for the preparation of (S)-tert-butyl-(methoxy(methyl)amino)-1-oxopropan-2-yl-carbamate, which, after reaction with the carbanion of derived from 2-chloro-6-methyl-N-phenylbenzamide, furnishes the intermediate.

At step 2, the intermediate is treated with hydrochloric acid in MeOH resulted in deprotection of the amine group and cyclization to form an isoquinolinone derivative. Subsequently, an aromatic nucleophilic substitution reaction between isoquinolinone derivative and 6-chloro-9-(tetrahydro-2H-pyran-2-yl)-9H-purine is carried out, that yields 8-chloro-2-phenyl-3-((1S)-1-(9-(tetrahydro-2H-pyran-2-yl)-9H-purin-6-ylamino)ethyl)isoquinolin-1(2H)-one.

Lastly, it treated with hydrochloric acid in ethanol to remove the THP protecting group, resulting in the formation of the phoshoinositide 3-kinase (PI3K) inhibitor, duvelisib.

Figure 2:
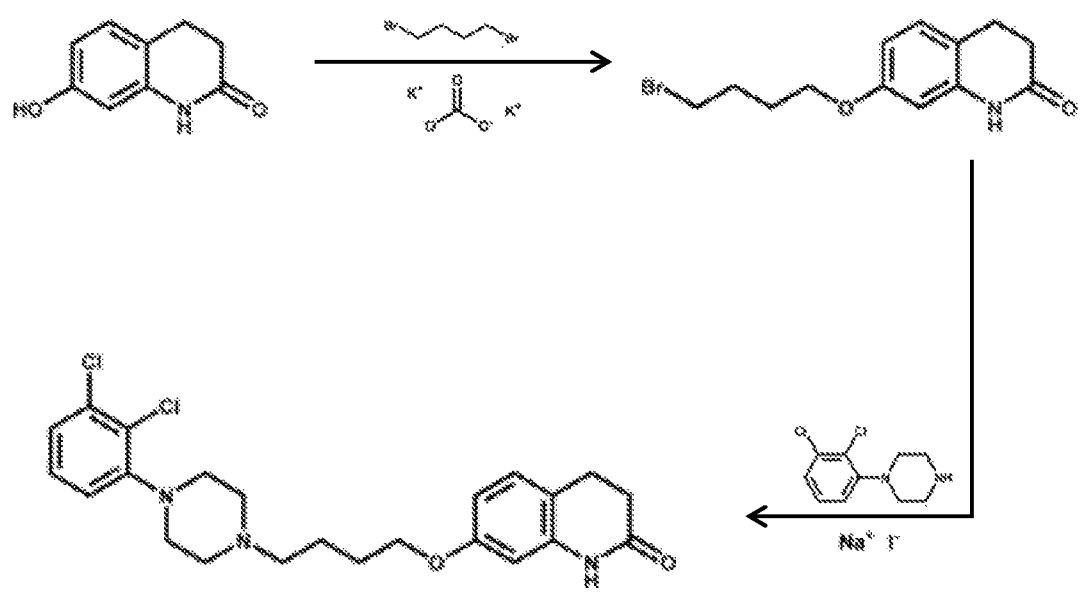
FIG. 2 is an illustration of chemical reactions related to synthesis of aripiprazole, in accordance with an embodiment of the present disclosure.

Referring to FIG. 2, illustrated are chemical reactions related to synthesis of aripiprazole, in accordance with an embodiment of present disclosure. synthesis of aripiprazole begins with alkylation of 7-hydroxy-3,4-dihydro-2(1H)-quinolinone by stirring it with 1,4-dibromobutane (3 molar equivalents) in the presence of potassium carbonate (1 molar equivalents) in dimethylformamide at 60° C. for four hours to give 7-(4-bromobutoxy)-3,4-dihydro-2(1 H)-quinolinone. The reaction mixture is then diluted with an equal volume of water, and the organic phase is extracted with ethyl acetate. After rotary evaporation, the resulting product is recrystallized in ethyl alcohol. The product is subsequently combined with sodium iodide (2 molar equivalents) in acetonitrile and refluxed for 30 minutes before cooling to room temperature. Subsequently, 1-(2,3-dichlorophenyl) piperazine (1.5 molar equivalents), and triethylamine (2 molar equivalents.) are added to the reaction mixture, and refluxed for another four hours. The resulting precipitate is filtered and discarded. The filtrate is evaporated in a low-pressure environment, and dissolved in ethyl acetate. Subsequently, the filtrate is washed, dried, and subjected to rotary evaporation to yield a resin. The resin is recrystallized in ethyl alcohol to provide the free base of aripiprazole as a white powdery substance. The powder may then be dissolved in ethyl alcohol with acid to yield a variety of salts.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A phosphoinositide 3-kinase inhibitor for use in the treatment of pancreatic cancer, wherein the phosphoinositide 3-kinase inhibitor is for use in combination therapy with an Src inhibitor.

2. The phosphoinositide 3-kinase inhibitor for use according to claim 1, wherein the phosphoinositide 3-kinase inhibitor is an inhibitor of the phosphatidylinositol 4,5-bisphosphate 3-kinase catalytic subunit gamma isoform and/or an inhibitor of the phosphatidylinositol 4,5-bisphosphate 3-kinase catalytic subunit delta isoform.

3. The phosphoinositide 3-kinase inhibitor for use according to claim 1, wherein the phosphoinositide 3-kinase inhibitor is duvelisib or a salt thereof.

4. The phosphoinositide 3-kinase inhibitor for use according to claim 3, wherein the treatment comprises oral administration of duvelisib or a salt thereof.

5. The phosphoinositide 3-kinase inhibitor for use according to claim 3, wherein the treatment comprises administration of duvelisib, or a salt thereof, at a daily dose of between 10 and 200 mg.

6. The phosphoinositide 3-kinase inhibitor for use according to claim 4, wherein the treatment comprises daily treatment with duvelisib, or a salt thereof, over a period of between 7 days and 8 weeks.

7. The phosphoinositide 3-kinase inhibitor for use according to claim 1, wherein the treatment involves treating a human subject that has higher expression of PIK3CG in tumour pancreatic tissue as compared to non-tumour pancreatic tissue.

8. The phosphoinositide 3-kinase inhibitor for use according to claim 2, wherein the Src inhibitor is aripiprazole or a salt thereof.

9. The phosphoinositide 3-kinase inhibitor for use according to claim 8, wherein the treatment comprises oral administration of aripiprazole or a salt thereof.

10. A pharmaceutical composition comprising a phosphoinositide 3-kinase inhibitor and an Src inhibitor.

11. The pharmaceutical composition according to claim 10, comprising duvelisib, or a salt thereof, and aripiprazole, or a salt thereof.

12. The phosphoinositide 3-kinase inhibitor for use according to claim 3, wherein the treatment comprises administration of duvelisib, or a salt thereof, at a daily dose of between 20 and 100 mg.

13. The phosphoinositide 3-kinase inhibitor for use according to claim 3, wherein the treatment comprises administration of duvelisib, or a salt thereof, at a daily dose of between 25 and 75 mg.

14. The phosphoinositide 3-kinase inhibitor for use according to claim 4, wherein the treatment comprises daily treatment with duvelisib, or a salt thereof, over a period of between 14 days and 8 weeks.

15. The phosphoinositide 3-kinase inhibitor for use according to claim 4, wherein the treatment comprises daily treatment with duvelisib, or a salt thereof, over a period of between 21 days and 6 weeks.

\* \* \* \* \*